United States Patent [19]

Toth et al.

[11] Patent Number: 4,551,465

[45] Date of Patent: Nov. 5, 1985

[54] PIPERIDINE DERIVATIVES AND PHARMACEUTICAL COMPOSITIONS CONTAINING THEM

[75] Inventors: Edit Toth; Jozsef Torley; Eva Palosi; Szabolcs Szeberenyi; Laszlo Szporny; Sandor Gorog; Istvan Hajdu, all of Budapest, Hungary

[73] Assignee: Richter Gedeon Vegyeszeti Gyar Rt., Budapest, Hungary

[21] Appl. No.: 565,902

[22] Filed: Dec. 27, 1983

[30] Foreign Application Priority Data

Dec. 28, 1982 [HU] Hungary .................................. 4185

[51] Int. Cl.$^4$ ................. C07D 295/08; A61K 31/445
[52] U.S. Cl. ..................................... 514/317; 546/241
[58] Field of Search ....................... 424/267; 546/241; 514/317

[56] References Cited

U.S. PATENT DOCUMENTS

| | | | |
|---|---|---|---|
| 3,272,841 | 9/1966 | DeWald | 546/241 |
| 3,647,863 | 3/1972 | Palopoli et al. | 546/241 |
| 4,094,908 | 6/1978 | Toth et al. | 546/241 |

FOREIGN PATENT DOCUMENTS 633816  1/1962  Canada ................................ 546/241

*Primary Examiner*—Norma S. Milestone
*Attorney, Agent, or Firm*—Karl F. Ross; Herbert Dubno

[57] ABSTRACT

The invention relates to new piperidine derivatives of the formula (I)

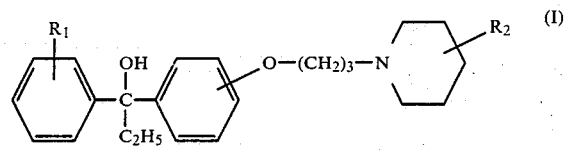

wherein
$R_1$ is halogen, trihalomethyl, alkyl having from one to 4 carbon atoms or alkoxy having from one to 4 carbon atoms; and
$R_2$ is hydrogen or alkyl having from one to 4 carbon atoms, and acid addition and quaternary ammonium salts thereof. According to another aspect of the invention there are provided processes for the preparation of these compounds. The compounds of the formula (I) are pharmacologically active. In particular, they inhibit the microsomal monooxigenase enzyme system of the liver. Pharmaceutical compositions containing them as active ingredient are also within the scope of the invention.

6 Claims, No Drawings

PIPERIDINE DERIVATIVES AND PHARMACEUTICAL COMPOSITIONS CONTAINING THEM

This invention relates to new piperidine derivatives and salts thereof. More particularly, the invention concerns new piperidine derivatives of the formula (I)

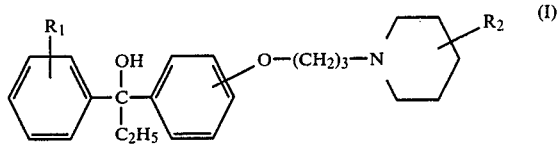

wherein
$R_1$ is halogen, trihalomethyl, alkyl having from one to 4 carbon atoms or alkoxy having from one to 4 carbon atoms; and
$R_2$ is hydrogen or alkyl having from one to 4 carbon atoms, and acid addition and quaternary ammonium salts thereof.

The invention further relates to processes for the preparation of these compounds and pharmaceutical compositions containing them as active ingredient.

The term "halogen" as used herein embraces all of the halogens, and may be fluorine, chlorine, bromine or iodine, preferably chlorine.

The term "alkyl having from one to 4 carbon atoms" refers to straight or branched chained aliphatic hydrocarbon groups containing from one to 4 carbon atoms.

The term "alkoxy having from one to 4 carbon atoms" is used herein to refer to straight or branched chained alkoxy groups containing from one to 4 carbon atoms.

The trihalomethyl groups may contain any of the halogens listed above.

Compounds of analogous structure are disclosed for example in the following references: C.A. 22, 410[1]; 40, 4712[5]; 35, 1781[2]; 42, P 1015 b; 47, 9548 e; 50, 12390 c; 50, 2509 i; 55, 17915 e; 55, 15413 b; 75, P 103682 b; 76, P 119921 k; 82, 16477 f; 90, 86082 f; 92, 52927 b. None of these citations mentions, however, any pharmaceutical activity of the disclosed compounds.

According to a further aspect of the present invention there is provided a process for the preparation of the compounds of the formula (I), wherein $R_1$ and $R_2$ each have the same meanings as defined above, and acid addition and quaternary ammonium salts thereof, which process comprises (a) reacting a propiophenone of the formula (II)

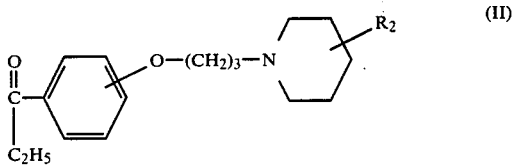

wherein $R_2$ is as defined above, with an organometallic compound of the formula (III)

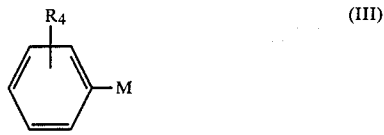

wherein $R_1$ is as defined above, and
M is an alkali metal, preferably lithium, sodium or potassium, or an MgX group, in which X is halogen; or (b) reacting a compound of the formula (IV)

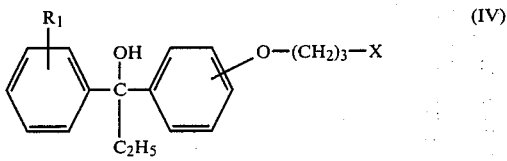

wherein $R_1$ is as defined above, and X is halogen, with an amine of the formula (V)

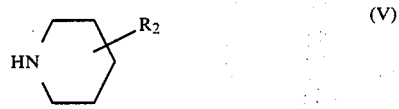

wherein $R_2$ is as defined above, preferably in the presence of an acid binding agent; or (c) reacting a benzophenone of the formula (VI)

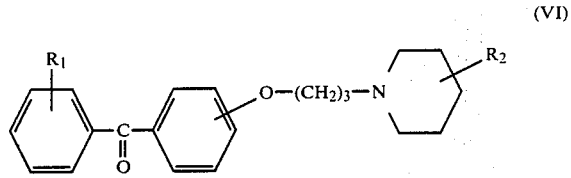

wherein $R_1$ and $R_2$ each have the same meanings as defined above, with an organometallic compound containing an ethyl group, preferably ethyl magnesium halide or ethyl lithium; or (d) reacting a propiophenone of the formula (VII)

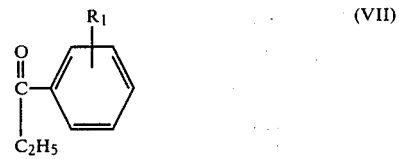

wherein $R_1$ is as defined above, with a Grignard compound of the formula (VIII)

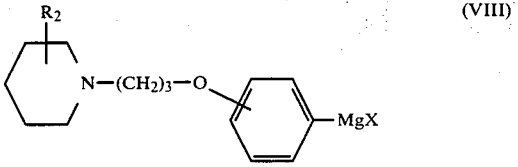

wherein $R_2$ is as defined above, and X is halogen; or
(e) reacting a compound of the formula (IX)

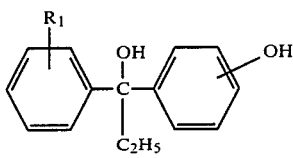

wherein R₁ is as defined above, preferably in the form of an alkali metal or quaternary ammonium phenolate thereof, with an amine of the formula (X)

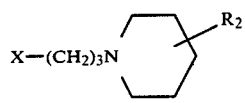

wherein R₂ is as defined above, and
X is halogen or an alkylsulfonyloxy or arylsulfonyloxy group,
or a salt thereof, preferably in the presence of an acid binding agent,
and if desired, converting any of the
products obtained by process variants (a) to (e) into their acid addition or quaternary ammonium salts, or converting a product obtained as an acid addition salt into a corresponding base and/or converting a free base into an acid addition or quaternary ammonium salt thereof.

According to a preferred embodiment of process variant (a) propiophenones of the formula (II) are reacted with the organometallic compounds of the formula (III), preferably appropriately substituted phenyl magnesium chlorides or bromides or an appropriately substituted phenyl lithium, in a dry inert organic solvent. The reaction is preferably carried out in an aprotic organic solvent, e.g. in an aliphatic ether such as diethyl ether, di-n-butyl ether or diethylene glycol dimethyl ether, an alicyclic ether such as tetrahydrofuran, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. nitrogen or argon. The reaction temperature may range from −60° C. up to the boiling point of the solvent, and preferably is between −30° C. and 100° C. When the reaction is complete, the reaction mixture is decomposed, preferably with an aqueous ammonium chloride solution, and the obtained compound of the formula (I) is separated. The product can be purified by known techniques, e.g. by distillation or crystallization.

According to process variant (b) a compound of the formula (IV), in which X preferably represents chloride or bromine, is reacted with a secondary amine of the formula (V). The reaction is preferably performed in an organic solvent, in the presence of a base suitable for binding the acid formed in the reaction. As a solvent for example hydrocarbons such as ligroin, benzene, toluene, halogenated hydrocarbons such as chloroform, ethers such as dioxane, alcohols such as ethanol, esters such as ethyl acetate, acid amides such as dimethyl formamide, ketones such as acetone, methyl isobutyl ketone, or a mixture of these solvents are employed. Suitable acid binding agents include for example inorganic or tertiary organic bases, but an excess amount of the amine of the formula (V) may also be used. If the excess of an amine of the formula (V) or a tertiary organic base is used to bind the hydrogen halide formed in the reaction, these may as well serve as solvents. The reaction can be carried out at a temperature between 20° C. and the boiling temperature of the solvent employed. When the reaction is complete, the product is isolated. This can be carried out for example by pouring the reaction mixture onto water, and isolating the product by solvent extraction. The organic phase is then washed halogen-free with water, dried and evaporated. The crude product can be purified for example by distillation or crystallization.

According to process variant (c) a benzophenone of the formula (VI) is reacted with an at least equimolar amount of an ethyl-containing organometallic compound, preferably ethyl magnesium bromide or ethyl magnesium iodide or ethyl lithium. The reaction is carried out in an inert dry organic solvent, as described in connection with process variant (a).

According to process variant (d) Grignard compounds of the formula (VIII), preferably containing bromine in place of X, are reacted with an at least equimolar amount of the propiophenones of the formula (VII), in a dry inert organic solvent, in a manner similar to that used in process variant (a).

According to a preferred embodiment of process variant (e) compounds of the formula (IX) are condensed with the tertiary amines of the formula (X) preferably in form of their alkali metal or quaternary ammonium phenolates. As a tertiary amine for example N-propyl-piperidino mesylate, tosylate, bromide or preferably chloride may be employed, as a free acid or optionally a salt, e.g. hydrogen halide thereof. The reaction is preferably carried out in an inert solvent, in the presence of an acid binding agent, under anhydrous conditions or in a mixture of water and an organic solvent. As organic solvents for example esters such as ethyl acetate, ethers such as dioxane, tetrahydrofurane or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (IX) can be converted into their phenolates by methods known in the art, e.g. using alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodides may be used. The reaction temperature may be varied within a wide range, and preferably is between 20° C. and the boiling point of the reaction mixture.

If desired, the compounds of the formula (I) can be converted into their acid addition salts or quaternary ammonium salts by methods known in the art. The acid addition salts can be prepared with inorganic and organic acids, e.g. hydrogen halides such as hydrochloric acid, hydrogen bromide, etc., sulfuric acid, propionic acid, phosphoric acids, formic acid, acetic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids such as methanesulfonic acid, arylsulfonic acids such as p-toluene-sulfonic acid, etc.

According to a preferred embodiment, the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture of these solvents, at a temperature between room temperature and the boiling point of the solvent. Th quaternary salts can be isolated for example by filtration and if desired, are purified by crystallization.

The starting compounds are known or can be prepared by methods known in the art.

The ketones of the formulae (II), (VI) and (VII) can for example be synthesized by the Friedel-Crafts type ketone synthesis (G. A. Olah: Friedel-Crafts and Related Reactions III/1, Ed.: Interscience Publishers 1964, pp. 1–63).

The compounds of the formulae (III) and (VIII) are for example prepared by preparing Grignard reactants from the corresponding aryl halides by known techniques (M. S. Kharash et al.: Grignard Reactions of Nonmetallic Substances, Ed., Prentice-Hall. Inc. (1954) pp. 5–90), while the alkali metal-organic compounds can be prepared following the method disclosed in Houben-Weyl: Methoden der Organischen Chemie, XIII/1, pp. 134–159 and 389–405 (1970).

The compounds of the formulae (IV) and (IX) can for example by synthetized by reacting the corresponding propiophenones with the corresponding Grignard reactants by methods known in the art (see e.g. M. S. Kharash et al.: Grignard Reactions of Nonmetallic Substances, Ed.: Prentice-Hall Inc. (1954) pp. 134–143).

The compounds of the formula (I) provided by the invention are pharmacologically active. In particular, they inhibit the liver microsomal monooxygenase enzyme system, and can therefore be used in therapy to inhibit or reduce the toxic effect of exogenic xenobiotic substances, which are transformed into toxic, active metabolites in the liver (D. M. Jerina et al.: Science, 185, 573 (1974)), causing liver necrosis, blood discrasia, carcinosis. In pharmaceutical combinations the compounds according to the invention may increase the duration of the effect of other active ingredients.

The enzyme inhibiting activity of the new compounds was tested in vivo, by measuring the change of hexobarbital oxidase activity. Female Hann.-Wistar rats, each weighing 50 to 60 g. were treated orally with a single 40 mg./kg. dose of the test compound. One and 24 hours after the administration of the active substance, the animals were narcotized with a 60 mg./kg. i.v. dosage of hexobarbital sodium, and the time elapsed until complete wakening was measured (Noordhock, J.: Eur. J. Pharmacol., 3, 242 (1968)). The data were recorded, and the mean values, the standard errors, as well as the percentage increase with respect to the controls were calculated for each group. As a reference compound Proadiphene[(2-diethylaminoethyl)-α,α-diphenyl valerate], i.e. the most effective known compound, was employed, in a dose of 100 mg./kg. The hexobarbital concentration of the plasm, measured on the instant wakening, was the same for both the treated and the control animals, and thus the increase of narcosis period was not due to a certain central nervous interaction (Jori, A. et al.: Biochem. Pharmacol., 19, 2687 (1970)). The results are shown in Table 1.

Abbreviations:

$\bar{x}$ = mean value
S.E. = standard error of the mean value
n = number of animals
The control group was treated with placebo.
A = 1-[3-[4[1(3-trifluoromethylphenyl)-1-hydroxypropyl]-phenoxy]-propyl]-piperidine
B = 4-methyl-1-[3-[4-[1-(2-methoxyphenyl)-1-hydroxypropyl]-phenoxy]-propyl]-piperidine

TABLE 1

| Compound | Dose (mg/kg) | Hexobarbital narcosis period in % of the control | | n |
|---|---|---|---|---|
| | | 1 hour | 24 hours | |
| Control | — | 100 ± 8.9 | 100 ± 10.8 | 10 |
| A | 40.0 | 129 ± 6.2 | 162 ± 3.8 | 10 |
| B | 40.0 | 144 ± 3.9 | 159 ± 8.5 | 10 |
| Proadiphene | 100.0 | 241 ± 9.6 | 44 ± 5.7 | 10 |

Control value ($\bar{x}$ ± S.E.) = 41.3 ± 3.67 min. (1)
48.12 ± 5.19 min. (2)

Both the increase of the narcosis period and the permanence of the effect (the compounds being effective even 48 hours after administration) indicate that the compounds of formula (I) inhibit the biotransformation of xenobiotic agents in the liver for a long time. The effect of the new compounds provided by the invention is better than that of Proadiphene also from qualitative aspects since, in contrast to Proadiphene, the initial inhibition effect caused by the compounds according to the invention is not followed by an increase, i.e. induction of the activity of the microsomal enzyme system.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)); metrazole spasm (Everett, G. M., Richards, R. K.: J. Pharmacol. Exp. Ther., 81, 402 (1944)); thiosemicarbazide spasm (Da Vanzo, J. P., Greig, M. E., Cormin, M. A.: Amer. J. Physiol., 201, 833 (1961)); strychnine spasm (Kerley, T. L., Richards, A. G., Begley, R. W., Abreu, B. B., Wesver, L. C.: J. Pharmacol. Exp. Ther., 132, 360, (1961)); nicotine spasm (Stone, C. A., Mecklenburg, K. L., Turnhans, M. L.: Arch. Int. Pharmacodyn., 117, 419 (1958)); rotarod test (Kinnard, W. J., Carr, C. J.: J. Pharmacol. Exp. Ther., 121, 354 (1957)); physostigmine lethality preventing effect (Nose, T. and Kojima, M.: Europl. J. Pharmacol., 10, 83 (1970)); yohimbine potentiation effect (Quinton, R. M.: Brit. J. Pharmacol., 21, 51 (1963)); and analgesic activity (Bianchi, C., Franceschini, J.: Brit. J. Pharm. Chemother., 9, 280 (1954)).

The compounds of the formula (I) when tested by the above methods proved completely ineffective, whereas Proadiphene exerted an anticonvulsive side effect (H. Ippen: Index Pharmacorum (1970), 40S 3.1).

The acute toxicity of the compounds of the formula (I) was tested on H-Wistar rats of both sexes, weighing 160 to 180 g. each. The compounds were administered in a single 500 mg./kg. dose, orally. The animals were observed for 14 days. The results are set forth in Table 2.

TABLE 2

| Compounds (500 mg./kg. p.o.) | Perished animals (%) |
|---|---|
| Proadiphene | 90 |
| A | 0 |
| B | 0 |

As appears from the data of Table 2, the toxicity of the instant compounds is considerably lower than that of Proadiphene, accordingly their therapeutic index is much more flavorable.

The pharmacologically active compounds according to the invention can be used in therapy in the form of pharmaceutical compositions which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectin or formaldehyde casein, etc. The formulations may also contain adhesives and lubricants such as talc, colloidal silica, stearin, calcium or magnesium stearate, etc.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in a suitable apparatus, and the granulate is dried. The remaining portion of the disintegrating substance, lubricant, antiadhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories which contain in addition to the active ingredient a carrier mass, called adeps pro suppository. Suitable carriers include vegetable fats, e.g. hardened vegetable oils, triglycerides of fatty acids having from 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable preparation, the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 1.0 and 200.0 mg./kg., preferably 2.0 and 40.0 mg./kg., which is preferably administered in many smaller units.

The invention will be further described with reference to the following illustrative Examples.

EXAMPLE 1

2-Ethyl-1-[3-[4-[1-(2-methoxyphenyl)-1-hydroxypropyl]-phenoxy]-propyl]-piperidine To 80 ml. of a 2.5 molar ethereal ethyl magnesium bromide solution a solution of 19.1 g. of 2-methoxy-4'-[3-(2-ethyl-piperid-1-yl)-propoxy]-benzophenone in 150 ml. of ether is added dropwise, with stirring at a temperature between 0° C. and 5° C., whereupon the reaction mixture is slightly boiled for one hour. After cooling the mixture is decomposed with a 10% aqueous ammonium chloride solution, and the aqueous phase is extracted with ether. The organic phase is washed to neutral with water, dried over anhydrous magnesium sulfate, and ether is distilled off under reduced pressure. Fractionation of the residue in vacuum yields 14.6 g. of the named compound, boiling at 224° to 226° C./13.3 Pa.

Analysis for $C_{26}H_{37}NO_3$: Calculated: C 75.87%, H 9.06%, N 3.40%; Found: C 75.71%, H 9.12%, N 3.48%.

EXAMPLE 2

1-[3-[4-[1-(3-Trifluoromethylphenyl)-1-hydroxypropyl]-phenoxy]-propyl]-piperidine 20.8 g. of α-ethyl-α-(3-trifluoromethyl)-4-(3-bromopropoxy)-benzylalcohol and 30 ml. of dry piperidine are slightly refluxed for two hours, whereupon piperidine is distilled off from the reaction mixture under reduced pressure, and the residue is extracted with benzene. The benzene phase is washed with water, dried over anhydrous magnesium sulfate and evaporated in vacuo. Crystallization of the residue from n-hexane yields 17.1 g. of the named compound, melting at 88° to 89° C.

Analysis for $C_{24}H_{30}F_3NO_2$: Calculated: C 68.39%, H 7.17%, F 13.52%, N 3.32%; Found: C 68.51%, H 7.30%, F 13.43%, N 3.25%.

Upon addition of hydrochloric acid in ether to an ethereal solution of the base under cooling, the corresponding hydrochloride is precipitated. Melting point: 186° to 188° C.

EXAMPLE 3

1-[3-[4-[1-(3-Trifluoromethylphenyl)-1-hydroxypropyl]-phenoxy]-propyl]-piperidine ethoiodide To a solution of 4.2 g. of the corresponding base with 20 ml. of acetone 1.2 ml. of ethyl iodide are added, and the reaction mixture is slightly boiled for two hours. After cooling the mixture is diluted with dry ether, and the precipitated crystalline quaternary salt is filtered off and dried. 5 g. of the named compound are obtained, melting at 124° to 125° C.

EXAMPLE 4

4-Methyl-1-[3-[4-[1-(2-methoxyphenyl)-1-hydroxypropyl]-phenoxy]-propyl]-piperidine To a Grignard reactant prepared from 1.82 g. of magnesium turnings and 14 g. of 2-bromoanisole in 50 ml. of dry tetrahydrofuran a solution of 14.5 g. of 4-[3-(4-methyl-piperidin-1-yl)propoxy]-propiophenone in 30 ml. of dry tetrahydrofuran is added dropwise, under moderate reflux. The reaction mixture is slightly boiled for 30 additional minutes. After cooling the mixture is decomposed with a 20% aqueous ammonium chloride solution, and the aqueous phase is extracted with tetrahydrofuran. The combined organic phases are washed with a saturated aqueous sodium chloride solution, dried over anhydrous magnesium sulfate, and evaporated in vacuo. Crystallization of the residue from a mixture of ethyl acetate and n-hexane yields 15.9 g. of the named compound, melting at 82° to 83° C.

Analysis for $C_{25}H_{35}NO_3$: Calculated: C 75.53%, H 8.87%, N 3.52%; Found: C 75.69%, H 8.96%, N 3.70%.

EXAMPLE 5

1-[3-[4-[1-(4-Chlorophenyl)-1-hydroxypropyl]-phenoxy]-propyl]-piperidine

To a Grignard reactant prepared from 1.82 g. of magnesium turnings and 22.3 g. of 4-[3-(piperidin-1-yl)-propoxy]-bromophenol in 100 ml. of dry tetrahydrofuran a solution of 8.4 g. of p-chloropropiophenone in 30 ml. of tetrahydrofuran is added dropwise, under slight reflux. The reaction mixture is slightly boiled for an additional hour, whereupon it is cooled and decomposed with a saturated aqueous ammonium chloride solution. The aqueous phase is extracted with tetrahydrofuran, the tetrahydrofuran phase is washed with a saturated aqueous sodium chloride solution, dried over anhydrous magnesium sulfate and evaporated to dryness in vacuo. Crystallization of the residue from a mixture of n-hexane and ethyl acetate yields 12.2 g. of the named compound, melting at 104° to 105° C.

Analysis for $C_{23}H_{30}ClNO_2$: Calculated: C 71.21%, H 7.79%, Cl 9.14%, N 3.61%; Found: C 71.40%, H 7.85%, Cl 9.25%, N 3.75%.

EXAMPLE 6

1-[3-[4-[1-(3-Chlorophenyl)-1-hydroxypropyl]-phenoxy]-propyl]-piperidine 7.9 g. of α-ethyl-α-(3-chlorphenyl)-4-hydroxybenzyl alcohol, 14 g. of anhydrous potassium carbonate and 6.6 g. of N-(3-chloropropyl)-piperidine hydrochloride in 80 ml. of methyl isobutyl ketone are boiled under moderate reflux for three hours. The solvent is distilled off under reduced pressure, to the residue water is added and it is extracted with benzene. The benzene phase is washed with an aqueous potassium hydroxide solution and subsequently with water, dried over anhydrous magnesium sulfate, and evaporated to dryness in vacuo. Crystallization of the residue from n-hexane yields 8.6 g. of the title compound, melting at 80° to 81° C.

Analysis for $C_{23}H_{30}ClNO_2$: Calculated: C 71.21%, H 7.79%, Cl 9.14%, N 3.61%; Found: C 71.11%, H 7.66%, Cl 9.31%, N 3.57%.

EXAMPLE 7

2-Ethyl-1-[3-[4-[1-(2-methoxyphenyl)-1-hydroxypropyl]-phenoxy]-propyl]-piperidine To 125 ml. of a 0.8 molar ethereal ethyl lithium solution a solution of 15.3 g. of 2-methoxy-4'-[3-(2-ethyl-piperid-1-yl)-propoxy]-benzophenone in 50 ml. of tetrahydrofuran is added dropwise, in argon atmosphere, with stirring at −15° C. The reaction mixture is stirred at room temperature for another two hours, whereupon it is decomposed with a saturated aqueous ammonium chloride solution under cooling. The aqueous phase is extracted with ether. The combined organic phases are washed with a saturated aqueous sodium chloride solution, and dried over anhydrous potassium carbonate. The solvent is distilled off under reduced pressure, and the residue is fractionated. 7.6 g. of the title compound are obtained. The physical characteristics of the product are identical with those given in Example 1.

EXAMPLE 8

1-[3-[4-[1-(2-Methoxyphenyl)-1-hydroxypropyl]-phenoxy]-propyl]-piperidine 7.7 g. of α-ethyl-α-(2-methoxyphenyl)-4-hydroxybenzylalcohol and 6.6 g. of N-(3-chloropropyl)-piperidine in 70 ml. of ethyl acetate, in the presence of 14 g. of anhydrous potassium carbonate and 0.5 g. of tetrabutyl ammonium hydrogensulfate are boiled under reflux for 8 hours. Thereafter the solvent is distilled off under reduced pressure, to the residue water is added, and it is extracted with ether. The ethereal phases are combined, washed with water, a 5% aqueous sodium hydroxide solution and again with water till neutral. The organic phase is dried over anhydrous potassium carbonate, and the solvent is distilled off under reduced pressure. Crystallization of the residue from ethyl acetate yields 9.5 g. of the named compound, melting at 110° to 111° C.

Analysis for $C_{24}H_{33}NO_3$: Calculated: C 75.16%, H 8.67%, N 3.65%; Found: C 74.97%, H 8.66%, N 3.78%.

EXAMPLE 9

From the new compounds according to the invention for example the following pharmaceutical compositions may be prepared.

| Tablets | |
|---|---|
| Composition of a single tablet: | |
| active ingredient | 100.0 mg. |
| lactose | 184.0 mg. |
| potato starch | 80.0 mg. |
| polyvinylpyrrolidone | 8.0 mg. |
| talc | 12.0 mg. |
| magnesium stearate | 2.0 mg. |
| aerosil (colloidal $SiO_2$) | 2.0 mg. |
| ultraamylopectin | 12.0 mg. |

From the above ingredients 400-mg. tablets are prepared by wet granulation and pressing. Active ingredient: 1-[3-[4-[1-(3-trifluoromethylphenyl)-1-hydroxypropyl]-phenoxy]-propyl]-piperidine.

Dragées

Tablets as described above are coated with a coating prepared from sugar and talc in a known manner. Dragées are polished with a mixture of bee wax and carnauba wax. Weight of a dragée: 500.0 mg.

Suppositories

Composition of a suppository:

| | |
|---|---|
| active ingredient | 100.0 mg. |
| lactose | 200.0 mg. |
| basic substance (e.g. Witepsol H) | 1700.0 mg. |

The basic substance is melted and cooled to 35° C. The active substance is thoroughly admixed with the lactose, and the mixture is homogenized in the basic substance in a homogenizator. The obtained mass is filled into cool molds. One suppository weighs 2000 mg.

Active ingredient: 1-[3-[4-[1-(3-trifluoromethyl-phenyl)-1-hydroxypropyl]-phenoxy]-propyl]-piperidine

Capsules

| Composition of a capsule: | |
|---|---|
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient and the additives are thoroughly blended, the mixture is passed through a 0.32-mm. sieve and filled into No. 4 hard gelatine capsules.

Active ingredient: 4-methyl-1-[3-[4-[1-(2-methoxyphenyl)-1-hydroxypropyl]-phenoxy]-propyl]-piperidine.

Suspension

Composition of 100 ml. of suspension:

| | |
|---|---|
| active ingredient | 1.00 g. |
| sodium hydroxide | 0.26 g. |
| citric acid | 0.30 g. |
| nipagin (4-hydroxybenzoic acid methyl-ester sodium salt) | 0.10 g. |
| Carbopol 940 (polyacrylic acid) | 0.30 g. |
| ethanol (96%) | 1.00 g. |
| raspberry aroma | 0.60 g. |
| sorbite (70% aqueous solution) | 71.00 g. |
| distilled water up to | 100.00 ml. |

To a solution of nipagin and citric acid in 20 ml. of distilled water Carbopol is added in small portions, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbite and an ethanolic raspberry aroma solution, with stirring. Active ingredient is added in small portions, and the mixture is homogenized. The suspension is supplemented with distilled water ad 100 ml., and the suspension syrup is passed through a colloidal mill.

Active ingredient: 4-methyl-1-[3-[4-[1-(2-methoxyphenyl)-1-hydroxypropyl]-phenoxy]-propyl]-piperidine.

We claim:

1. A compound of the Formula (I)

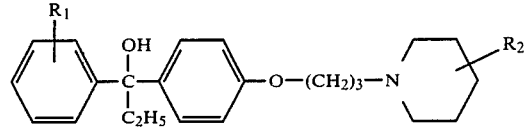

wherein
R$_1$ is halogen, trihalomethyl, C$_1$–C$_4$ alkyl, or C$_1$–C$_4$ alkoxy; and
R$_2$ is hydrogen or C$_1$–C$_4$alkyl, or a pharmaceutically acceptable acid addition or quaternary ammonium salt thereof.

2. 1-[3-[4-[1-(3-trifluoromethylphenyl)-1-hydroxypropyl]-phenoxy]-propyl]-piperidine or a pharmaceutically acceptable acid addition or quaternary ammonium salt thereof as defined in claim 1.

3. 4-methyl-1-[3-[4-[1-(2-methoxyphenyl)-1-hydroxypropyl]-phenoxy]-propyl]-piperidine or a pharmaceutically acceptable acid addition or quaternary ammonium salt thereof as defined in claim 1.

4. A pharmaceutical composition for inhibiting the liver microsomal monooxygenase enzyme system containing a pharmaceutically effective amount of the compound of the formula (I) as claimed in claim 1, wherein R$_1$ and R$_2$ are as defined in claim 1, or a pharmaceutically acceptable carrier.

5. A method of inhibiting the liver microsomal monooxygenase enzyme system in a susceptible subject which comprises administering an effective amount of a compound as defined in claim 1.

6. A compound selected from the following group:
2-ethyl-1-[3-[4-[1-(2-methoxyphenyl)-1-hydroxypropyl]-phenoxy]-propyl]-piperidine and salts thereof;
1-[3-[4-[1-(3-trifluoromethylphenyl)-1-hydroxypropyl]-phenoxy]-propyl]-piperidine and salts thereof;
4-methyl-1-[3-[4-[1-(2-methoxyphenyl)-1-hydroxypropyl]-phenoxy]-propyl]-piperidine and salts thereof;
1-[3-[4-[1-(4-chlorophenyl)-1-hydroxypropyl]-phenoxy]-propyl]-piperidine and salts thereof;
1-[3-[4-[1-(3-chlorophenyl)-1-hydroxypropyl]-phenoxy]-propyl]-piperidine and salts thereof; and
1-[3-[4-[1-(2-methoxyphenyl)-1-hydroxypropyl]-phenoxy]-propyl]-piperidine and salts thereof.

* * * * *